United States Patent
Vincent et al.

(10) Patent No.: US 11,608,822 B2
(45) Date of Patent: *Mar. 21, 2023

(54) DIAPHRAGM ASSEMBLY FOR A PULSATILE FLUID PUMP

(71) Applicant: VentriFlo, Inc., Pelham, NH (US)

(72) Inventors: Douglas E. Vincent, Pelham, NH (US); George Koenig, Nashua, NH (US); James W. Poitras, St. Cloud, FL (US); Matthew J. Murphy, Marshfield, MA (US)

(73) Assignee: VentriFlo, Inc., Pelham, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,247

(22) Filed: Jan. 11, 2022

(65) Prior Publication Data

US 2022/0268266 A1    Aug. 25, 2022

Related U.S. Application Data

(63) Continuation of application No. 17/182,893, filed on Feb. 23, 2021, now Pat. No. 11,236,741.

(51) Int. Cl.
*F04B 43/02* (2006.01)
*A61M 60/268* (2021.01)
(Continued)

(52) U.S. Cl.
CPC ........... *F04B 43/02* (2013.01); *A61M 60/109* (2021.01); *A61M 60/268* (2021.01);
(Continued)

(58) Field of Classification Search
CPC .... F04B 43/02; A61M 60/268; A61M 60/894; A61M 60/40; A61M 2230/04;
(Continued)

(56) References Cited

U.S. PATENT DOCUMENTS

| 2,954,738 A | 10/1960 | DiVette |
| 4,290,347 A * | 9/1981 | Basch ................. F02M 37/046 417/471 |

(Continued)

OTHER PUBLICATIONS

International Searching Authority—International Search Report, pertaining to International Application No. PCT/US2021/19253, dated Nov. 12, 2021, together with the Written Opinion of the International Searching Authority, 14 pages.

*Primary Examiner* — Dominick L Plakkoottam
(74) *Attorney, Agent, or Firm* — Sunstein LLP

(57) ABSTRACT

A diaphragm assembly for a pulsatile fluid pump includes an edge-mounted flexible diaphragm, the diaphragm configured for operation cyclically between a diastole mode and a systole mode. The diaphragm assembly further includes a systolic distribution brace having an interior wall configured to cup a portion of the outside surface of the diaphragm, and a diastolic plate, embedded in the diaphragm, mechanically coupled to a portion of the inside surface of the diaphragm.

(Continued)

In the course of the systole mode, force is applied across the maximum radial extent of the systolic distribution brace, so as to impart tension in the diaphragm around the periphery of the systolic distribution brace. In the course of the diastole mode, force is applied across the maximum radial extent of the diastolic plate, so as to impart tension in the diaphragm around the diastolic plate.

6 Claims, 4 Drawing Sheets

(51) Int. Cl.
  *A61M 60/109* (2021.01)
  *A61M 60/837* (2021.01)
  *F04B 43/00* (2006.01)
  *A61M 60/894* (2021.01)
(52) U.S. Cl.
  CPC ....... *A61M 60/837* (2021.01); *F04B 43/0054* (2013.01); *A61M 60/894* (2021.01)
(58) Field of Classification Search
  CPC ............ A61M 60/50; A61M 2205/122; A61M 2205/3334; A61M 60/274
  See application file for complete search history.

(56) References Cited

U.S. PATENT DOCUMENTS

| | | | | |
|---|---|---|---|---|
| 4,360,324 | A * | 11/1982 | Ohara | A61M 60/837 |
| | | | | 417/388 |
| 4,541,788 | A * | 9/1985 | Nomura | F04B 9/04 |
| | | | | 417/471 |
| 5,006,104 | A * | 4/1991 | Smith | A61M 60/427 |
| | | | | 600/16 |
| 5,011,380 | A * | 4/1991 | Kovacs | H01F 7/1615 |
| | | | | 417/413.1 |
| 5,092,879 | A | 3/1992 | Jarvik | |
| 5,186,615 | A * | 2/1993 | Karliner | F04B 43/067 |
| | | | | 417/387 |
| 5,349,896 | A | 9/1994 | Delaney, III et al. | |
| 5,513,956 | A * | 5/1996 | Lewis | A61M 60/585 |
| | | | | 417/415 |
| 6,814,547 | B2 * | 11/2004 | Childers | A61M 5/445 |
| | | | | 210/321.71 |
| 6,953,323 | B2 | 10/2005 | Childers et al. | |
| 11,236,741 | B1 * | 2/2022 | Vincent | F04B 43/0054 |
| 2003/0217962 | A1 * | 11/2003 | Childers | A61M 1/288 |
| | | | | 210/257.2 |
| 2013/0336825 | A1 * | 12/2013 | Nonomura | F04B 43/0054 |
| | | | | 417/472 |

* cited by examiner

DIAPHRAGM ASSEMBLY FOR A PULSATILE FLUID PUMP

RELATED APPLICATIONS

The present application is a continuation application of and claims priority to U.S. patent application Ser. No. 17/182,893, entitled "Diaphragm Assembly for a Pulsatile Fluid Pump" and filed on Feb. 23, 2021, which itself is related to three U.S. patent applications bearing serial nos. 17/182,915, 17/183,067, and 17/183,080, all filed on Feb. 23, 2021. Each of the foregoing applications is hereby incorporated herein by reference in its entirety.

TECHNICAL FIELD

The present invention relates to pulsatile fluid pumps, and more particularly to pulsatile fluid pumps suitable for pumping blood.

BACKGROUND ART

A pulsatile fluid pump is taught in U.S. Pat. No. 7,850,593 ("our prior patent") for an invention of Douglas Vincent and Matthew Murphy, who are co-inventors of the present invention. Our prior patent discloses a pump actuated by a linear motor configured to cause reciprocation of a flexible membrane, serving as a wall of a fluid housing, that is in turn coupled to a pair of ball valves, in a manner as to implement pulsatile fluid flow.

SUMMARY OF THE EMBODIMENTS

In accordance with one embodiment of the invention, a diaphragm assembly for a pulsatile fluid pump includes an edge-mounted flexible diaphragm having an inside surface for contacting a fluid to be pumped, an outside surface exposed to ambient air, the diaphragm configured for operation cyclically between a diastole mode and a systole mode. The diaphragm assembly further includes a systolic distribution brace having a maximum radial extent and having an interior wall configured to cup a portion of the outside surface of the diaphragm, and a diastolic plate, embedded in the diaphragm, having a maximum radial extent and mechanically coupled to a portion of the inside surface of the diaphragm. The maximum radial extent of the systolic distribution brace at a periphery thereof is greater than the maximum radial extent of the diastolic plate. Further, the systolic distribution brace, the diastolic plate, and the diaphragm are mechanically linked to each other, so that: (i) in the course of the systole mode, the diaphragm overhangs the periphery of the systolic distribution brace and force is applied across the maximum radial extent of the systolic distribution brace, so as to impart tension in the diaphragm around the periphery of the systolic distribution brace; and (ii) in the course of the diastole mode, force is applied across the maximum radial extent of the diastolic plate, so as to impart tension in the diaphragm around the diastolic plate, wherein the differing radial extents of the systolic distribution brace and the diastolic plate produce differing distributions of force on the diaphragm over the course of these two modes, so as to distribute stress on the diaphragm and reduce strain on the diaphragm over the course of a pumping cycle.

Alternatively or in addition, the diaphragm has a reinforcing layer disposed between the systolic distribution brace and the diastolic plate.

Also alternatively or in addition, the systolic distribution brace has a rounded outer edge, and the diaphragm is configured to roll beyond the maximum radial extent of the systolic distribution brace and over the rounded outer edge.

Further alternatively or in addition, the interior wall of the systolic distribution brace that is configured to cup the portion of the outside surface of the diaphragm is disposed at an obtuse angle.

Also alternatively or in addition, the diastolic plate has a bevel. Alternatively or in addition, the diastolic plate has a bevel at an angle corresponding generally to the obtuse angle of the interior wall of the systolic distribution brace.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
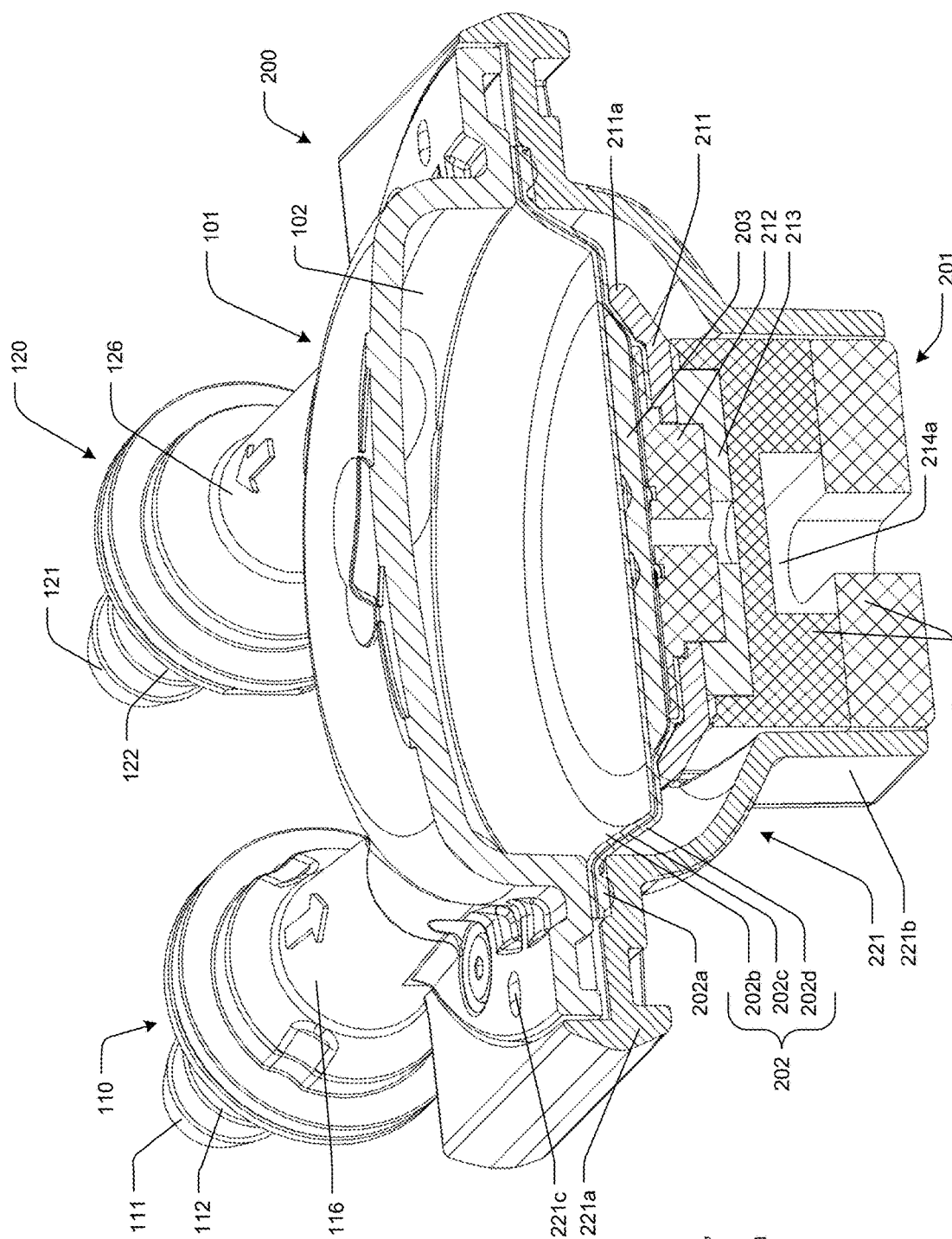
FIG. 1 is a vertical section of an integral pump assembly 200 showing a diaphragm assembly 201 mounted to a pump-valving assembly 101 in diastole mode, in which the chamber 102 is being filled.

Definitions. As used in this description and the accompanying claims, the following terms shall have the meanings indicated, unless the context otherwise requires:

A "set" includes at least one member.

"Diastole mode" is a phase of operation of a pulsatile pump, according to embodiments of the present invention, during which the diaphragm 202 of the pump-valving assembly 101 is pulled away from the chamber 102 so as to create negative pressure within the chamber 102, inlet ball check valve assembly 110, and third tapered tract 126, but not the fourth tapered tract 122

"Systole mode" is a phase of operation of a pulsatile pump, according to embodiments of the present invention, during which the diaphragm 202 is pushed towards the chamber 102, so as to create positive pressure within the chamber 102, outlet ball check valve assembly 120, and the second tapered tract 116, but not the first tapered tract 112.

FIG. 1 is a vertical section of an integral pump assembly 200 showing a diaphragm assembly 201 mounted to a pump-valving assembly 101 in diastole mode, in which the chamber 102 is being filled. As stated in U.S. patent application Ser. No. 17/183,080, filed Feb. 23, 2021 ("the 1004 application"), which is incorporated herein by reference in the Related Applications section above, the integral pump assembly 200 is configured to be removably coupled to a control housing 361 described and shown in the 1004 application, and the diaphragm assembly 201 is configured to be removably coupled to a linear motor 330 described and shown in the 1004 application. Among other things, the pump-valving assembly 101 includes an inlet ball check valve assembly 110 and an outlet ball check valve assembly 120. The integral pump assembly 200 includes a pump housing 221 including a neck 221b in which the coupler 214 reciprocates as the diaphragm 202 reciprocates. The neck 221b is configured to maintain axial alignment of the coupler 214 and (via physical features, such as flattened sides) is also configured to maintain rotational alignment of the coupler 214. The pump-valving assembly 101 is discussed in further detail in the related application, referenced above, bearing. As the diaphragm 202 is pulled down (in a direction away from the chamber 102) to cause filling of the chamber 102, it creates a negative pressure that draws fluid into the chamber 102 through the inlet port 111. Similarly, as the diaphragm 202 is pushed up in a direction into the chamber 102, it creates a positive pressure that causes flow of the fluid out of the chamber 102 through the outlet port 121. (In these figures, like numbered items correspond to similar components across different figures.)

The edge mount 202a diaphragm 202 (consisting of inside surface 202b, reinforcing layer 202c, and outside surface 202d) is part of a diaphragm assembly 201 including, among other things, diastolic plate 203, attachment stem 212, systolic distribution brace 211, and retaining ring 213. The diastolic plate 203 is embedded within the diaphragm 202, over the reinforcing layer 202c and mechanically coupled to the inside surface 202b of the diaphragm 202 and to the attachment stem 212. As the diaphragm assembly 201 is pulled down to fill the chamber 102, force is transmitted through the coupler 214 via the coupler slot 214a to the attachment stem 212 to the diastolic plate 203, which, in turn, exerts force on the reinforcing layer 202c to minimize stress on the elastomeric inside surface 202b and elastomeric outside surface 202d of the diaphragm 202. The attachment stem 212 is also coupled to the systolic distribution brace 211 through retaining ring 213. The outer diameter of the diastolic plate 203 is smaller than the diameter of the interior of the rounded outer edge 211a of the systolic distribution brace 211. Construction of the diaphragm assembly 201 therefore is not symmetric for pulling and pushing. In pulling, through the attachment stem 212 and the diastolic plate 203, stress is placed on a more concentrated portion of the diaphragm 202 (defined largely by the diameter of the diastolic plate 203) than in pushing, which occurs more broadly through the attachment stem 212 and the systolic distribution brace 211, which has a larger diameter than the diastolic plate 203 and is configured to cup the diaphragm 202.

Through its expected useful life, the diaphragm 202 must tolerate millions of strokes. With each stroke, the diaphragm 202 is subjected to physical movement and oscillation between positive and negative pressures within the chamber 102. In order to increase life expectancy, the ideal diaphragm 202 should be as thin as possible, because thin materials minimize bending stresses during flexure. A thin elastomeric material, used for the inside surface 202b and outside surface 202d of the diaphragm 202, has excellent flexibility, but low tensile strength. This low tensile strength causes the elastomeric material to excessively strain during the oscillating positive and negative pressures seen during operation, eventually leading to failure. The reinforcing layer 202c provides the tensile strength required to withstand these pressure fluctuations while maintaining the flexibility of the elastomeric layers 203 and 202d.

Figure 2:
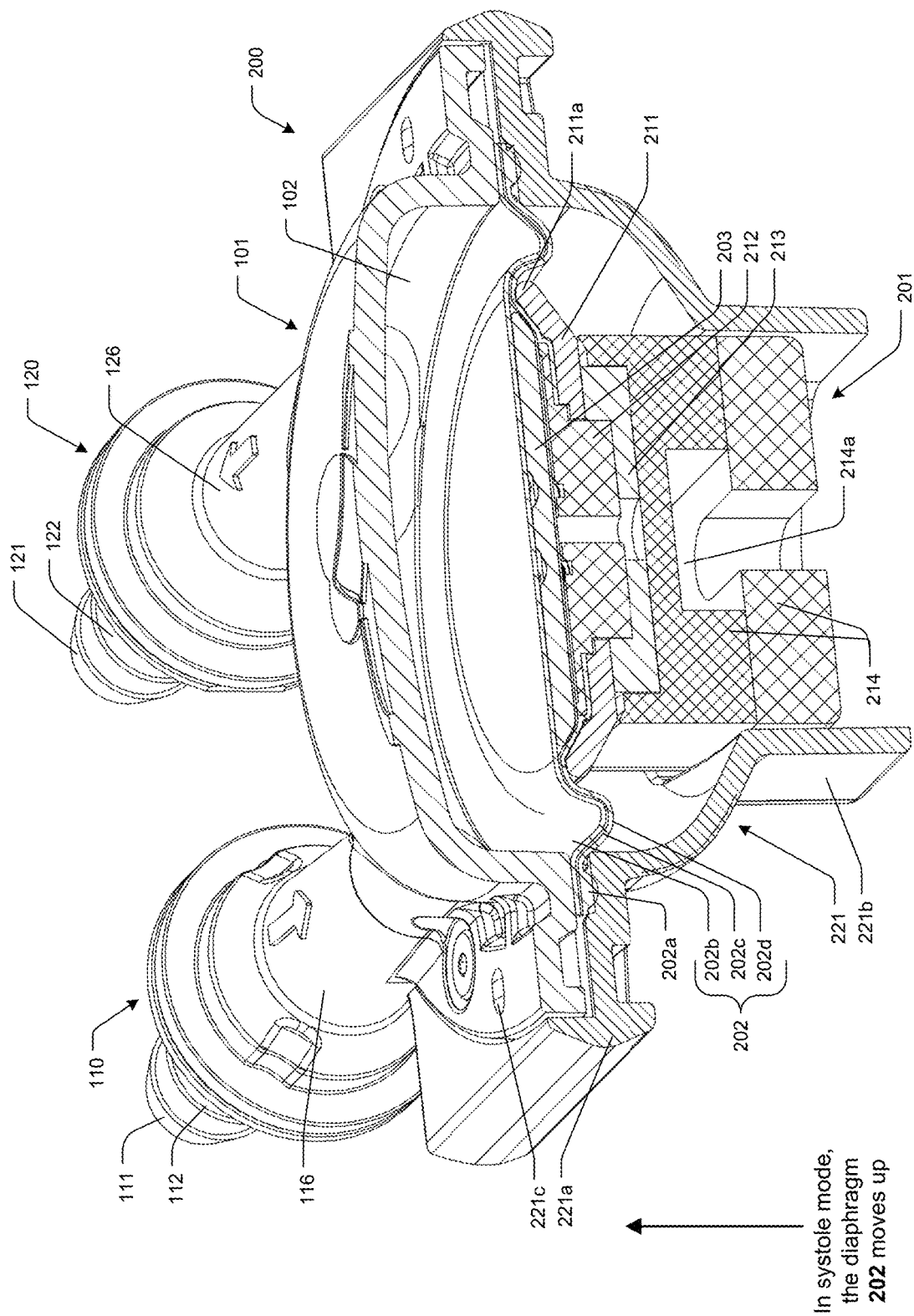
FIG. 2 is a vertical section of an integral pump assembly 200 showing a diaphragm assembly 201 mounted to a pump-valving assembly 101 in systole mode, in which the chamber 102 is being emptied.

FIG. 2 is a vertical section of an integral pump assembly 200 showing a diaphragm assembly 201 mounted to a pump-valving assembly 101 in systole mode, in which the chamber 102 is being emptied. The systolic distribution brace 211 is mounted beneath the diaphragm 202 and mechanically coupled to the diastolic plate 203 through the attachment stem 212. As the diaphragm assembly 201 is pushed up to empty the chamber 102, force is transmitted through the coupler 214 via the coupler slot 214a to both the retaining ring 213 (and on to the systolic distribution brace 211) and to the systolic distribution brace 211 directly, which systolic distribution brace 211 cups and exerts force on the diaphragm 202 (including the reinforcing layer 202c), distributing the stress over a changing area of the diaphragm 202 as it wraps around the rounded outer edge 211a of the systolic distribution brace 211, reducing strain on the diaphragm 202 over the course of a pumping cycle, and thereby increasing its life.

Figure 3:
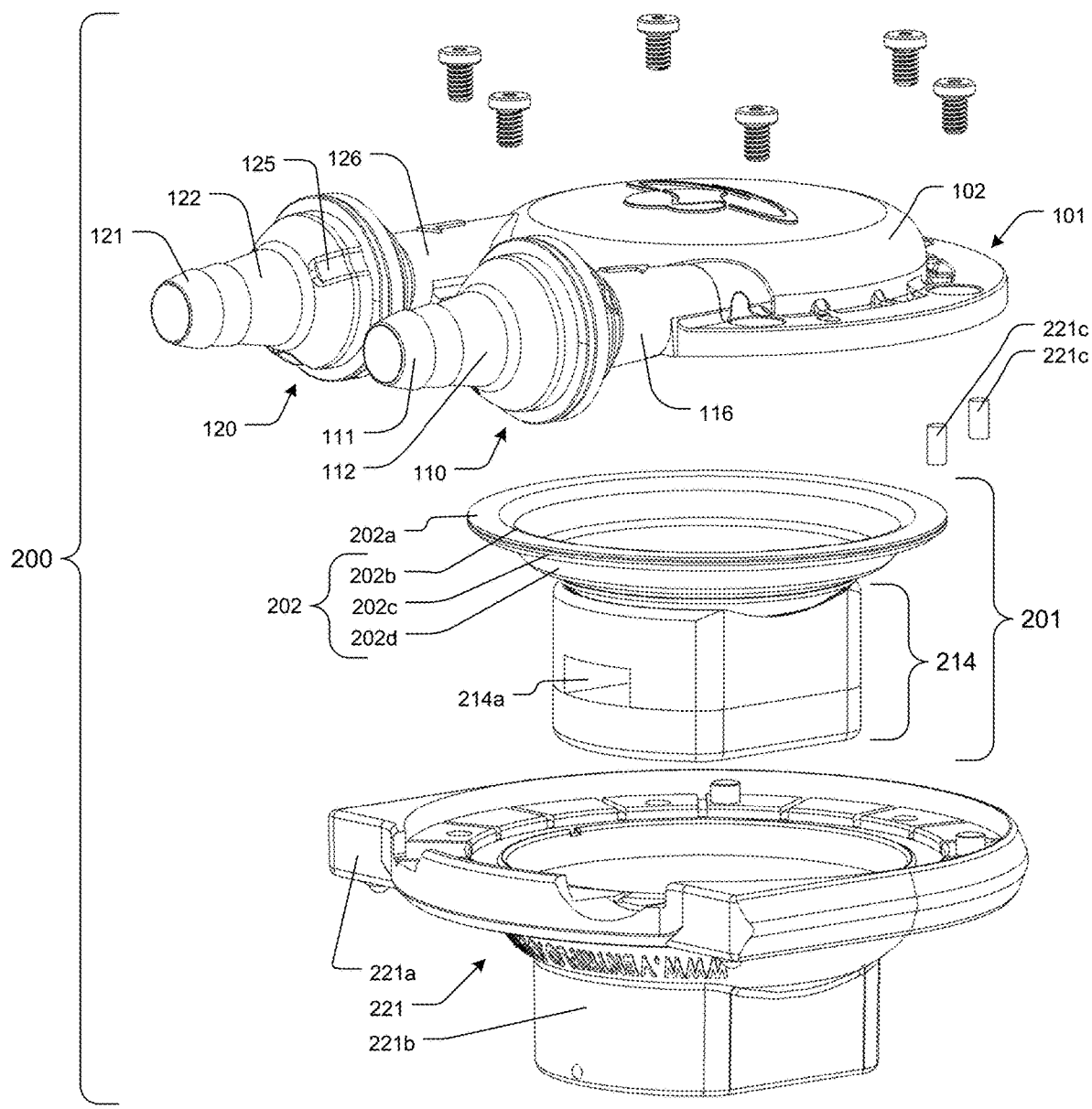
FIG. 3 is an exploded perspective view, from the side, of an integral pump assembly 200 showing a pump-valving assembly 101, diaphragm assembly 201, and peripheral flange 221*a*.

FIG. 3 is an exploded perspective view, from the side, of an integral pump assembly 200, showing a pump-valving assembly 101, chamber 102, inlet port 111, first tapered tract 112, second tapered tract 116, outlet port 121, fourth tapered tract 121, outlet rib 125, third tapered tract 126, diaphragm assembly 201, edge mount 202a diaphragm 202 (composed of inside surface 202b, reinforcing layer 202c, and outside surface 202d), pump housing 221 (with peripheral flange 221a, neck 221b, and compliant member 221c. Items 101-126 are discussed in further detail in the related application, referenced above, bearing.

Figure 4:
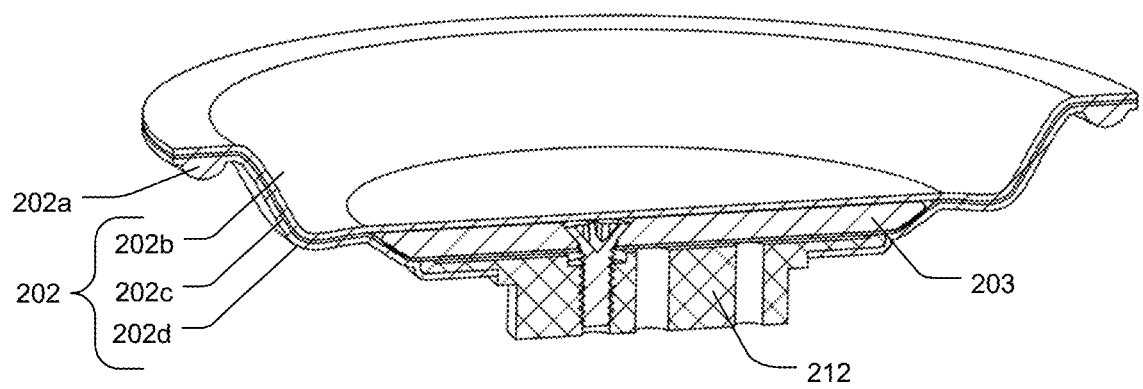
FIG. 4 is a vertical section of a diaphragm 202.

FIG. 4 is a vertical section of a diaphragm 202 (composed of edge mount 202a, inside surface 202b, reinforcing layer 202c, and outside surface 202d), also showing the diastolic plate 203 and attachment stem 212.

The structure of a pulsatile pump in accordance with various embodiments of the present invention can usefully reflect attributes of the human heart. The human heart is preload sensitive—the heart cannot "pull" blood into the left ventricle; it can only allow the blood available to flow naturally into the ventricle. The human heart is also afterload sensitive in that it is responsive to the compliance and resistance in the downstream vasculature and doesn't exert excess force on the blood, which could damage the vasculature. Lastly, the left ventricle cannot deliver blood that isn't in the ventricle when it contracts; there is a limited bolus of blood that it can deliver.

The pump-valving assembly 101 has similar attributes of inherent safety: it is preload and afterload sensitive, and it is limited in both the volume of blood it can deliver and the force at which it can deliver that bolus of blood. When filling, the pump-valving assembly 101 allows gravity filling from the venous reservoir, exerting minimal negative pressure. When the chamber in the pump-valving assembly 101 is emptying, the linear motor that powers the pump valving assembly is limited by design. In consequence the pump valving assembly cannot overpressure the downstream tubing or vasculature, instead delivering less than the volume of blood in the pump chamber 102, thereby only delivering as much volume as the vasculature can receive.

The pump-valving assembly 101 is analogous to a left ventricle of the human heart; the inlet ball check valve assembly 110 used in various embodiments hereof is analogous to a mitral valve; and the outlet ball check valve assembly 120 used in various embodiments hereto is analogous to an aortic valve. Like the human heart, the inlet 110 and outlet 120 ball check valve assemblies are passive and require a slight reversal of flow to close. This slight reversal of flow mimics the slight reversal that occurs when the aortic valve of the human heart closes.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A diaphragm assembly for a pulsatile fluid pump comprising:
   an edge-mount flexible diaphragm having an inside surface for contacting a fluid to be pumped, an outside surface exposed to ambient air, the diaphragm configured for motion cyclically in an axial direction between a diastole mode and a systole mode;
   a systolic distribution brace having a maximum radial extent and having an interior wall configured to cup a portion of the outside surface of the diaphragm;
   a diastolic plate, embedded in the diaphragm, having a maximum radial extent and mechanically coupled to a portion of the inside surface of the diaphragm;
   wherein (i) the maximum radial extent of the systolic distribution brace at its periphery is greater than the maximum radial extent of the diastolic plate; (ii) the systolic distribution brace is configured to embrace a majority of an axial extent of the diastolic plate; and (iii) the systolic distribution brace, the diastolic plate, and the diaphragm are mechanically linked to each other.

2. A diaphragm assembly according to claim 1, wherein the diaphragm has a reinforcing layer disposed between the systolic distribution brace and the diastolic plate.

3. A diaphragm according to claim 1, wherein the systolic distribution brace has a rounded outer edge and the diaphragm is configured to roll beyond the maximum radial extent of the systolic distribution brace and over the rounded outer edge.

4. A diaphragm assembly according to claim 1, wherein the interior wall of the systolic distribution brace that is configured to cup the portion of the outside surface of the diaphragm is disposed at an obtuse angle.

5. A diaphragm assembly according to claim 1, wherein diastolic plate has a bevel.

6. A diaphragm assembly according to claim 1, wherein diastolic plate has a bevel at an angle corresponding generally to the obtuse angle of the interior wall of the systolic distribution brace.

* * * * *